United States Patent [19]

Siegel

[11] 4,137,453

[45] Jan. 30, 1979

[54] METHODS AND APPARATUS FOR IMPROVING ELECTRON CAPTURE DETECTORS BY COLLECTION OF IONS

[75] Inventor: Melvin W. Siegel, Pittsburgh, Pa.

[73] Assignee: Extranuclear Laboratories, Inc., Pittsburgh, Pa.

[21] Appl. No.: 719,280

[22] Filed: Aug. 31, 1976

[51] Int. Cl.$^2$ .............................................. G01T 1/18
[52] U.S. Cl. ................................ 250/382; 250/384; 250/385
[58] Field of Search ............... 250/381, 385, 374, 389

[56] References Cited
U.S. PATENT DOCUMENTS

| 3,154,680 | 10/1964 | Greene | 250/381 |
| 3,601,609 | 8/1971 | Yauger | 250/375 |

Primary Examiner—Harold A. Dixon
Attorney, Agent, or Firm—Mason, Mason and Albright

[57] ABSTRACT

Method and apparatus for the detection of electronegative chemical species in gas flows, such as exist from gas chromatographs, by sampling the detector volume via an aperture connecting to a lower pressure region containing apparatus to collect and measure the negative ion current. Because of the free diffusion of electrons in the region of the aperture, as opposed to ambipolar diffusion in a conventional electron capture detector volume, the electrons are largely removed from the negatively charged components in the gas stream there. Similarly, positive ion current may be measured, thus extending the analytical capability of the invention to classes of chemical species normally not yielding a response in electron capture detectors.

43 Claims, 15 Drawing Figures

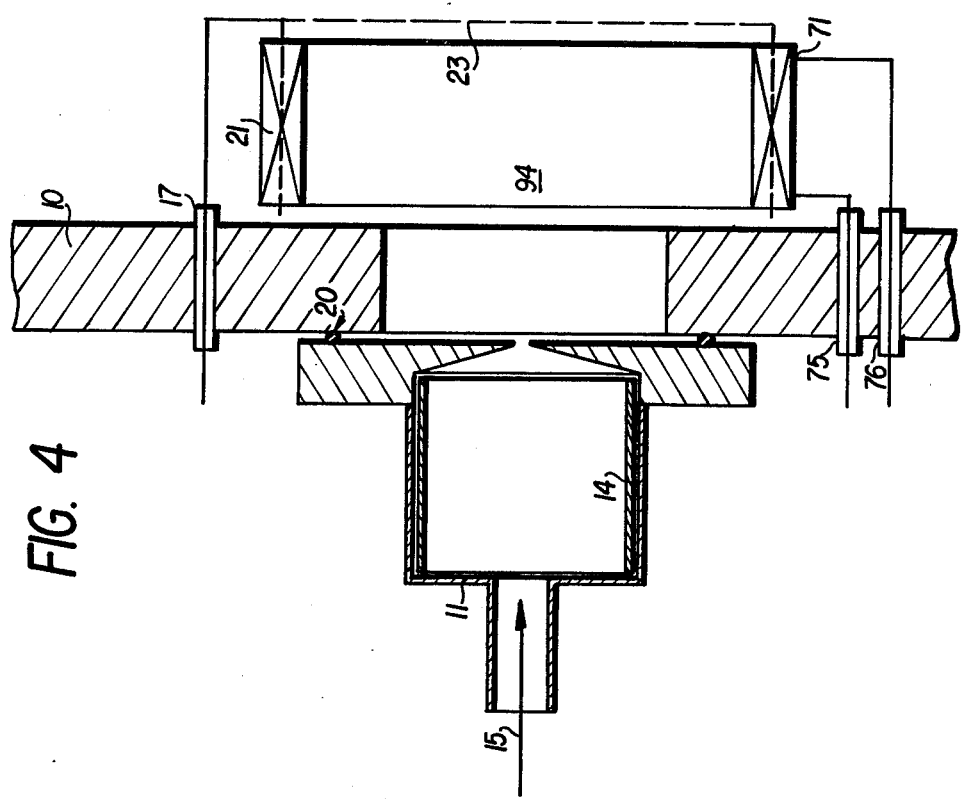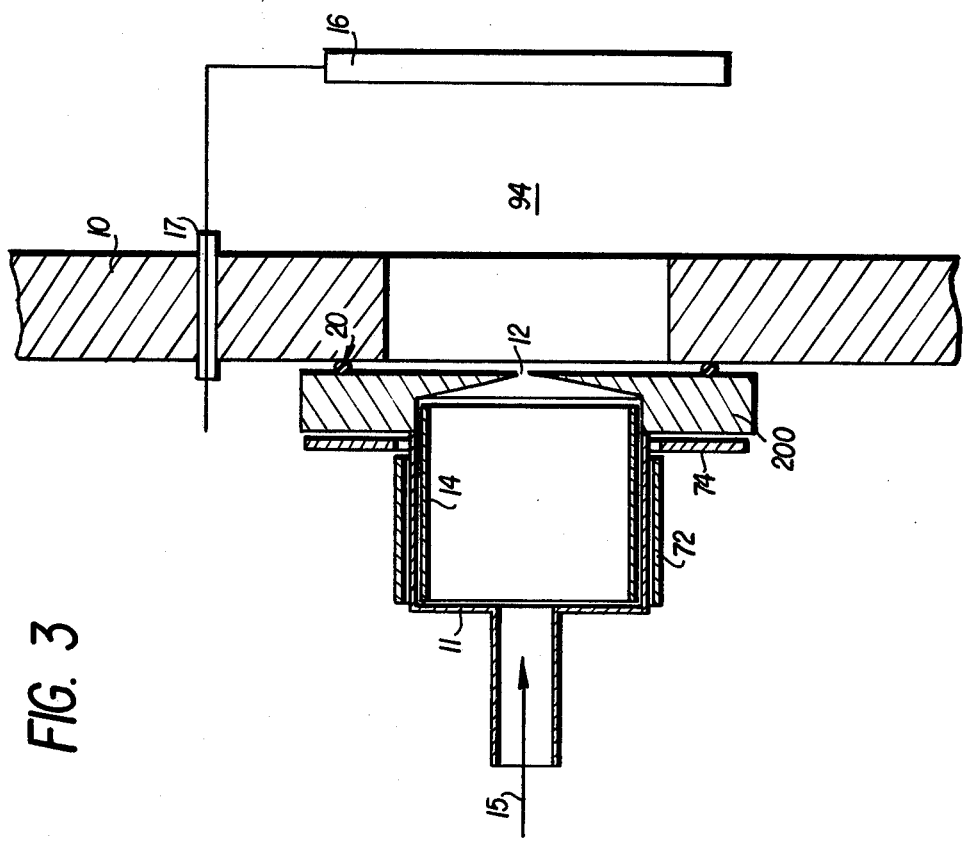

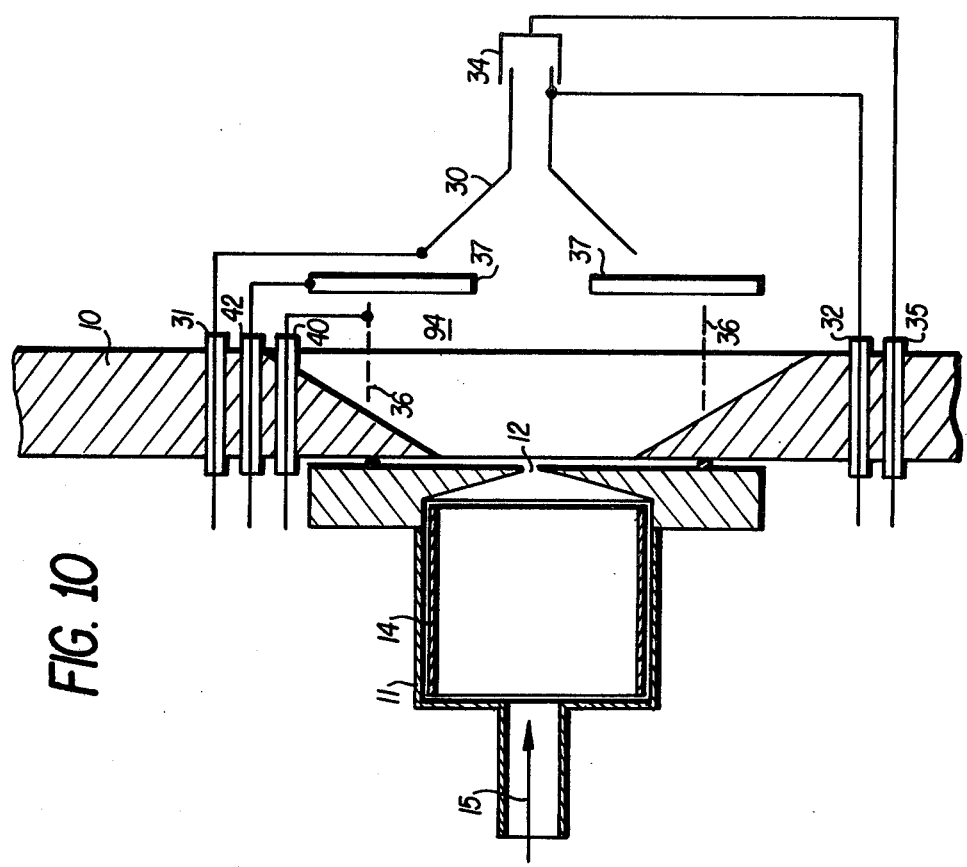
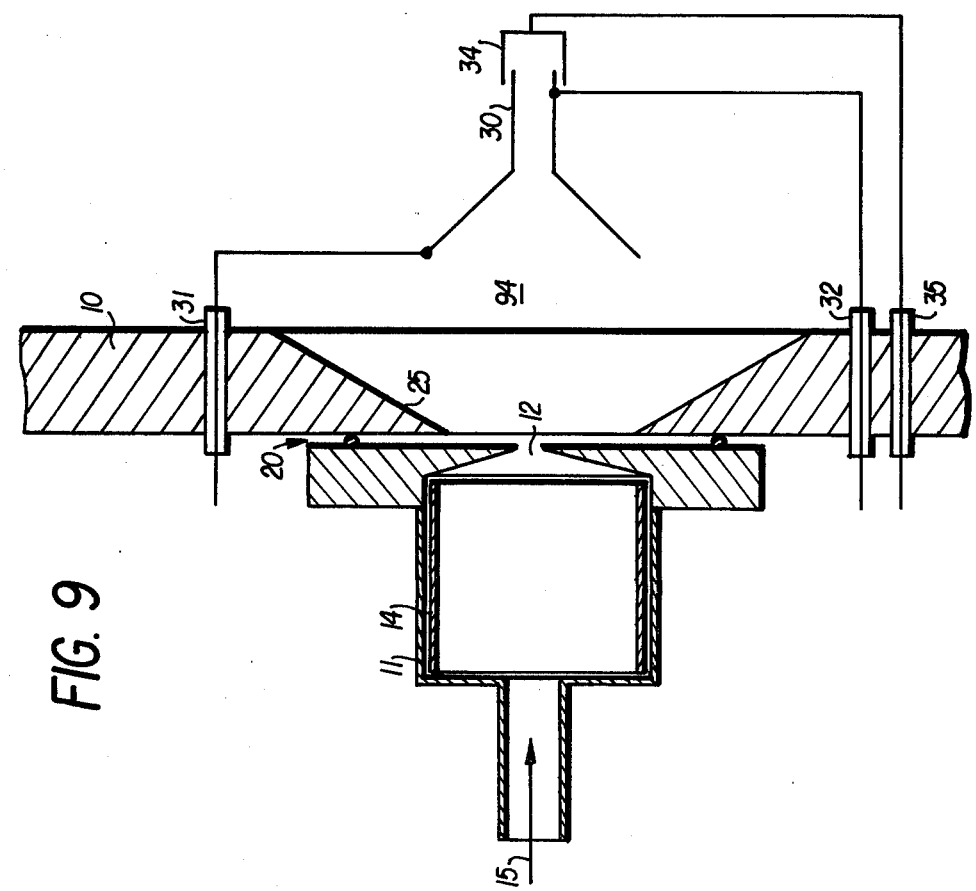

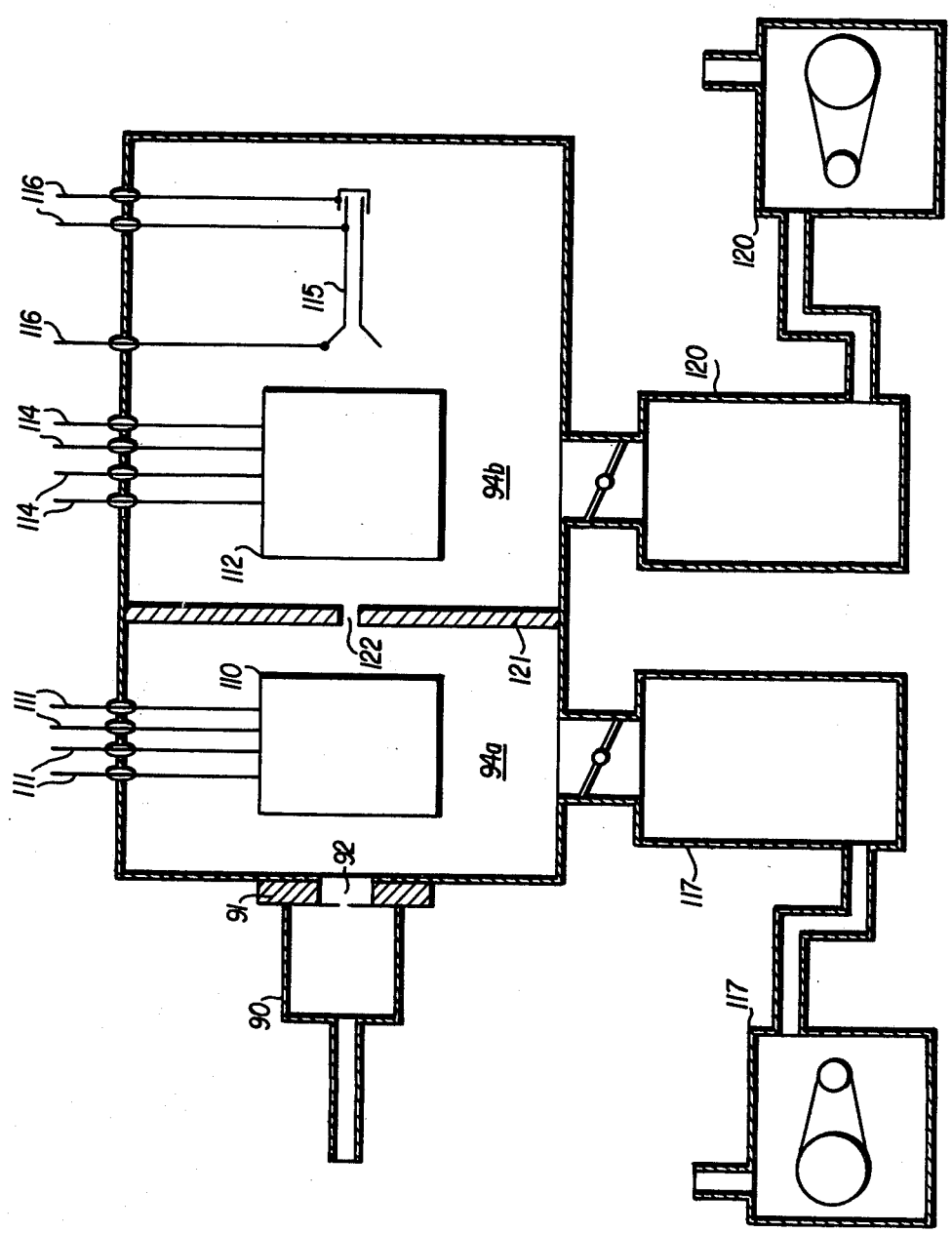

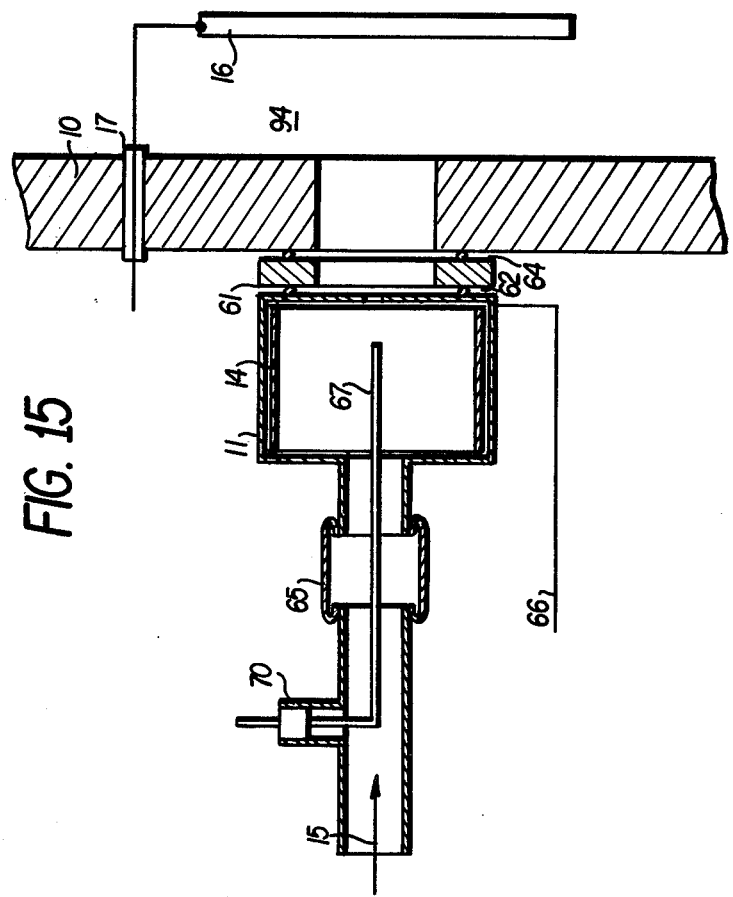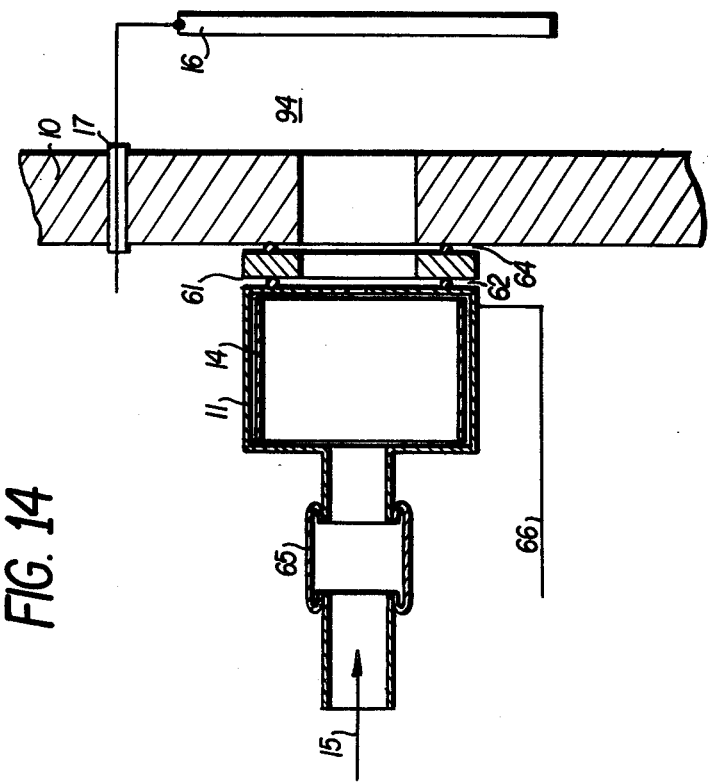

METHODS AND APPARATUS FOR IMPROVING ELECTRON CAPTURE DETECTORS BY COLLECTION OF IONS

BACKGROUND OF THE INVENTION

(1) Field of the Invention

The invention relates to a new type of electron capture detector (ECD) for measuring the concentration of trace sample materials in a carrier gas stream such as the eluent of a gas chromatograph. An important improvement provided by this invention is that smaller trace sample concentrations are detectable, that is, the ultimate sensitivity is substantially improved. Also an improved dynamic range of quasi-linear response to sample concentration results, and there is an improved stability against drift and aging. Furthermore, with this invention the applicability of ECD-type devices is extended to classes of chemical species which form positive ions but not negative ions and thus are not detected in conventional electron capture detectors.

(2) Discussion of the Prior Art

Electron capture detectors (ECD) are employed as highly sensitive detectors for trace quantities of molecular species having large reaction rates for forming negative ions in an inert gas plasma at about atmospheric pressure. Many species of environmental interest, such as pesticide residues, fall into this class. The ECD is typically employed to measure the concentration as a function of time of such species in a flowing carrier gas stream. Most often the carrier gas stream is the eluent from a gas chromatograph column.

Essential features of ECDs in conventional prior art embodiments include a well defined and temperature controlled reaction volume through which the sample bearing carrier gas flows at a controlled rate, a source of ionization within this volume (for example a quantity of appropriately confined $^{63}$Ni or $^3$H radiating $\beta$-rays which produce the required carrier gas plasma), and a pair of electrodes (generally delimiting the active volume) for the purpose of collecting mobile charged particles from the active volume when an appropriate voltage is applied between the electrodes. Auxiliary apparatus includes an instrument to measure the current flowing in response to the applied voltage, and a source of the collection voltage, which may be either dc or pulsed.

The measured current when electron capturing species are absent is called the standing current. In the prior art, response to an electron capturing sample concentration is observed as a decrease in the current to a value smaller than the standing current. In a variant technique, the collection voltage is applied intermittently as pulses of fixed amplitude and duration, repeating at the feedback controlled frequency required to collect a preselected constant average current. In this mode of operation, increases in pulse frequency rather than decreases in current are measured. For simplicity, whenever changes in current are referred to in the description which follows, it should be appreciated that alternatively, corresponding changes in pulse repetition frequency when the ECD is used in this variant form, may be involved.

The current observed in the presence of sample molecules is smaller than in the absence of same because the sample molecules capture electrons, forming negative ions. The reason that electron capture causes a decrease in observed current is not well understood; a popular explanation is that since the negative ions have a smaller mobility than the electrons they are collected more slowly than the electrons and so have greater opportunity than electrons to be destroyed by recombination with positive ions.

A major problem with conventional prior ECD embodiments is that the response to sample is observed as a relatively small decrease in current superimposed on a much larger standing current. The smallest detectable sample concentration can thus be no smaller than that determined by the requirement that the response exceed the inherent noise level of the device, such inherent noise level being proportional to the square root of the standing current. Thus, if the dynamic range of the EDC is increased by, for example, increasing the strength of the radioactive source, the electron concentration is increased and so is the absolute noise level. It has occurred to the inventor that a preferable mode of operation would be one in which some other parameter is monitored, this parameter having value zero (rather than a maximum) at zero sample concentration, and such parameter increasing (rather than decreasing) in proportion to increasing sample concentration. That is, it is considered that a preferable mode of operation requires measuring a characteristic of the device which has a derivative with respect to sample concentration that is a positive constant, and which has a value of at zero sample concentration of zero. These preferred characteristics are provided by the invention disclosed herein, in which the negative ion density is directly measured.

Another problem occurring with conventional embodiments is that they provide a measure only of the total quantity of electron capturing sample molecules present and do not otherwise distinguish these molecules. Several embodiments of the present invention provide mass spectrometric identification of the electron capturing species. Furthermore, in such embodiments employing mass spectrometric identification, the nature of the positive ions is easily examined, thus extending the applicability of the technique to non-electron capturing species.

SUMMARY OF THE INVENTION

The gas flowing out of the reaction volume of an ECD carries entrained with it the plasma of positive ions, electrons, and negative ions characteristic of their equilibrium distribution in the reaction volume. The source of this plasma is most often an appropriately distributed quantity of the radioactive isotope $^{63}$Ni, the $\beta$-rays of which, in losing their energy to the carrier gas, each generate on the average approximately 600 positive ions of the carrier gas and 600 thermal energy electrons. Alternate sources of the required plasma include $\alpha$-rays, $\beta$-rays from other sources, $\gamma$-rays, other photons, and electrons as from a corona discharge.

When this gas and plasma are retained at near or above atmospheric pressure, the plasma rapidly decays by recombination of positive ions with electrons and with negative ions, and by diffusion of ions and electrons to nearby surfaces. In contrast, when the gas and plasma are passed through a pinhole aperture of finite thickness into a region of lower pressure, then: (1) with typical aperture dimensions of approximately 25 $\mu$m diameter by 25 $\mu$m thickness, the vast majority of electrons are lost by free diffusion to the walls of the aperture; (2) the vast majority of positive and negative ions pass, with the carrier gas, into the vacuum; (3) with sufficiently high capacity vacuum pumps, the gas density and ion density in the lower pressure region become sufficiently small so that positive ion-negative ion recombination practically ceases; and (4) appropriately placed and biased electrodes in the lower pressure region collect either the negative ions only, or the positive ions only, or both negative and positive ions separately, and these individual ion currents are measurable.

The pressure in the higher pressure ionization region is in most instances maintained with ± 20% of atmospheric pressure, but in certain specific cases where doing so enhances performance or satisfies an interfacing requirement with other apparatus it is advantageous to maintain in this region a selected pressure in a range of up to 100 atmospheres to as low as 0.1 torr.

This invention is concerned primarily with measurement of negative ion current in the above described arrangement. The collected current of negative ions (amperes) is equal to the concentration of negative ions in the active volume (cm$^{-3}$), multiplied by the volumetric gas flow rate through the active volume (cm$^3$ sec$^{-1}$), and multiplied by the electronic charge (1.6 × 10$^{-19}$ coulombs). The concentration of negative ions in the active volume is proportional to the concentration of sample molecules in the gas stream entering the active volume. Thus, the derivative of the negative ion current with respect to sample concentration is a positive constant, and the value of the negative ion current at zero sample concentration is zero. This satisfies the previously defined criteria for a positive quantity to measure and improve ECD ultimate sensitivity by decreasing the inherent noise level in the measured quantity.

For the detection and measurement of positive ions emerging from the aperture, current detection via mass spectrometry is incorporated into the electron capture detector arrangement described.

The instant invention takes advantage of the circumstance that the noise level associated with a measurement of negative ion current into a vacuum is independent of the electron concentration in the ECD and depends in principle only on the statistics of the negative ion current fluctuations. Thus the ECD electron concentration (and ECD dynamic range) is favorably increased by increasing the radioactive source strength, while at the same time little or no price is exacted in ultimate sensitivity.

Of importance to the functioning of the claimed device in the manner described is the ability of a small aperture in a gas stream strongly to attenuate the concentration of free electrons in the gas stream while only weakly attenuating the concentration of negative and positive ions therein. In a volume characteristic of typical ECD devices, and with a radioactive source of sufficient activity to raise the positive ion concentration above approximately 10$^7$ cm$^{-3}$ (this being satisfied in all conventional ECD devices), the diffusion rates of electrons and ions are coupled by their space charge interaction, the result being that electrons and ions diffuse at equal rates, each of their effective diffusion constants becoming equal to twice the diffusion constants of the positive ions in isolation. This phenomena is called "ambipolar diffusion." Under conditions of ambipolar diffusion the charged particle concentrations adjust themselves via their mutual interaction so that net charge neutrality is the rule, meaning the positive ion concentration must equal the sum of the negative ion and electron concentrations. These conditions of charge neutrality and equality of effective diffusion constants need not, and indeed cannot, hold true within short distances of boundary surfaces, the relevant scaling length being the Debye length which is well-known and is given by the formula $$\lambda_D = \sqrt{kT_e \epsilon_0 / 4\pi n e^2}$$

where $T_e$ is the electron temperature (under conditions described usually equal to the gas temperature) k is Boltzmann's constant in J K$^{-1}$, $\epsilon_0$ is the permittivity of vacuum in farad m$^{-1}$, e is the electron charge in coulombs, and n is the electron concentration in number per m$^3$, the result $\lambda_D$ then being in meters.

Within approximately one Debye length of a surface, charge inequality is the rule, the resulting strong electrostatic fields serving to isolate the plasma from the enclosing walls. In a volume having characteristic dimensions comparable to the Debye length, the ions and electrons then diffuse at different rates. Since the typical dimensions of the apertures employed in this invention are 25 $\mu$m diameter by 25 $\mu$m thickness, and since the Debye length characteristic of the ECD plasma is the order of 50 $\mu$m, it follows that in passing through the aperture the electrons diffuse to the aperture walls very rapidly, while the ions diffuse so slowly as to be only imperceptibly attenuated. This effect is enhanced by choosing, from among several aperture types having the same gas conductance, one having a diameter and length which maximize the attenuation of electron concentration while minimizing the attenuation of ion concentration.

An important aspect of the invention is that for improved precision in an ECD, it is preferable to measure the negative ions rather than the electrons because the negative ion concentration increases in proportion to the electronegative sample molecule concentration and thus represents a source of information having lower inherent noise than the electron concentration. In this invention the negative ions are separated from the electrons by flowing the eluent of the active region, by means of a gas pressure difference, through a small aperture, in which aperture the electrons diffuse to the walls sufficiently rapidly that they are effectively eliminated, whereas the ion concentration is negligibly attenuated. A further aspect of the invention is that in this embodiment the positive ions, rather than or in addition to the negative ions, may also be observed, thus yielding quantitative analytical information concerning concentrations of molecules of chemical species not normally detectable in the ECD.

At very low sample concentrations the current of residual electrons escaping through the aperture may nevertheless be comparable to or greater than the negative ion current. In such cases, it is advantageous as a further improvement to employ a magnetic field in the ion collection region, its strength and direction being chosen spatially to separate the electrons and negative ions by virtue of the differing curvatures assumed by negative ions and electrons.

Alternatively, in place of or in addition to a magnetic field, it is advantageous to employ a mass spectrometer as a current detecting element, thus conveniently separating the residual electron current from the negative ion current, as well as determining the negative ion and positive ion currents according to the masses of the ions present.

Other objects, adaptabilities and capabilities of the invention will be appreciated as the description progresses, reference being had to the accompanying drawings, in which:

BRIEF DESCRIPTION OF THE DRAWINGS

FIG. 3 is a diagrammatic representation of a further form of the invention wherein a carrier gas containing trace concentrations of materials which capture electrons in an atmospheric pressure plasma passes through a reaction chamber containing a radioactive source (which produces said plasma in the carrier gas), the gas and plasma then passing through a pinhole aperture into a lower pressure region where negative ions are collected by an electrode. Alternatively, trace concentrations of materials which do not capture electrons strongly may be detectable in this configuration via certain modifications they cause in the positive ion current.

FIG. 4 is a diagrammatic representation of a similar form of the invention in which the electrode is constructed of mesh that it may more easily pass the gas flow while subtending a larger solid angle as seen from the aperture. Also, shown in the FIG. 4 is a coil for generating an axially directed magnetic field to suppress residual electrons not removed by passage through the aperture; alternatively the source of magnetic field may be oriented to produce a transverse magnetic field to separate ions and electrons physically in the manner of a low resolution magnetic mass spectrometer;

FIG. 9 is a diagrammatic representation of a similar form of the invention wherein the collection electrode is replaced with a particle multiplier of the continuous or discrete dynode type to serve as an ion current amplifier or allow counting of individual ions at very low signal levels. In this embodiment and in further embodiments employing the particle multiplier the lower pressure chamber is maintained approximately $10^{-5}$ torr or less.

FIG. 10 is a diagrammatic representation of a similar form of the invention in which one or more electrostatic lens elements are inserted between the aperture and particle multiplier to allow ions to be efficiently collected and focused on the sensitive face of the particle multiplier.

FIG. 11 is a general diagrammatic representation of an apparatus wherein the lower pressure chamber is divided into two individually pumped subchambers connected by a differential pumping aperture having a diameter in the range 1 mm to 1 cm This embodiment allows operation of focusing optics in the first subchamber at a pressure lower than the pressure in the ECD active volume, such pressure nevertheless still being too high for operation of the particle multiplier, whereas in the second subchamber the pressure is maintained at $10^{-5}$ torr or less and is therefore suitable for the operation of the particle multiplier and, optionally, other devices such as optical elements and mass spectrometers. In embodiments employing a mass spectrometer the positive ion spectrum may be examined and so used to detect and quantify the concentration of chemical species which do not capture electrons, while the negative ion spectrum similarly provides more detailed information than is available via total negative ion current alone.

FIG. 14 is a diagrammatic representation of a similar form of the invention in which insulating materials isolate the reaction volume from the electrical potential of the vacuum system ("ground") and the gas supply system, whereby the reaction chamber is operable at an elevated potential to establish emerging ion energy with respect to a ground-referenced detection system.

FIG. 15 is a diagrammatic representation of a similar form of the invention which includes an additional electrode, depicted in the form of an axial wire, in the reaction chamber whereby the ECD is operable in its conventional current collecting manner as well as in the manner described herein.

DESCRIPTION OF THE PREFERRED EMBODIMENTS

Figure 1:
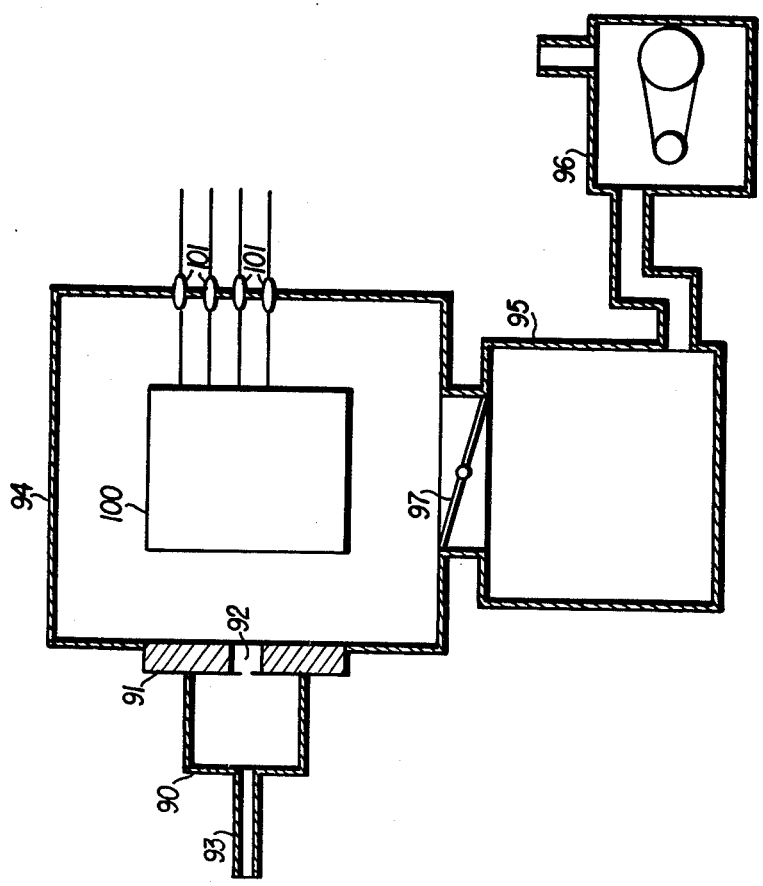
FIG. 1 is a diagrammatic representation which illustrates a general form of the invention wherein an electron capture detector is provided with a small aperture through which the effluent of its active volume flows into a region of lower pressure (depicted as a chamber partially evacuated by a vacuum pumping arrangement) there being located inside the chamber a current collecting apparatus electrically connected to the external environment by means of feedthroughs.

Referring to FIG. 1, a generalized embodiment of the basic invention is illustrated wherein an electron capture detector 90 with a conventional gas inlet 93, has affixed thereto flange 91 incorporating an aperture 92. By means of flange 91, the electron capture detector 90 is attached to a hermetically sealed chamber 94 in which a pressure lower than the pressure in the electron capture detector 90 is maintained by means of apparatus such as, but not restricted to, a diffusion pump 95, backed by a mechanical pump 96. Such apparatus for maintaining a lower pressure in chamber 94 is separated from said chamber 94 by means of a valve 97 which is controlled outside chamber 94. Within chamber 94 a current collecting apparatus 100 is provided with the necessary electrical connections leading to the external environment such as electrical feedthroughs 101.

In operation, a gas entering inlet 93 is subjected to radiation from a radioactive source or other appropriate means to produce a plasma with positive ions, electrons and negative ions entrained therein in a manner characteristic of their equilibrium distribution in the reaction volume. The pressure in the detector 90 being higher than that within chamber 94, the gas and plasma pass through aperture 92 having dimensions as heretofore described so that most of the electrons diffuse into the flange 91 via the walls of aperture 92 thus destroying the plasma. Most of the negative ions are received by the collecting apparatus 100 creating a current which is registered and measured in a manner well known to the art. The combination of the diffusion pump 95, the mechanical pump 96 and valve 97 regulate the absolute pressure within the chamber 94 so that it is suitable for its particular function — at say $10^{-5}$ torr or less.

Figure 2:
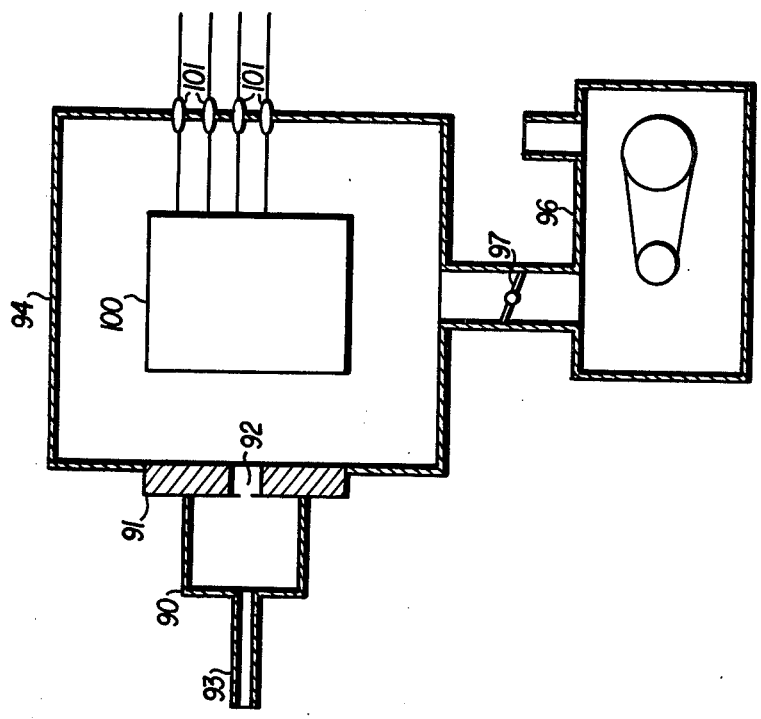
FIG. 2 is a further diagrammatic representation of a similar form of the invention wherein only a mechanical pump is employed.

In FIG. 2 an embodiment similar to that illustrated in FIG. 1 is shown in which only a mechanical pump 96 is employed. It will be understood that the embodiment in FIG. 2 operates essentially the same as that of FIG. 1 except that there is some sacrifice in the capability to maintain a uniform and high vacuum within the chamber 94.

A simplified embodiment of the invention is illustrated in FIG. 3 wherein a carrier gas flow 15 passes into and through a reaction chamber 11 and thence through a pinhole aperture 12 which may be integral with or demountable from reaction chamber 11, and finally into a vacuum region behind a wall 10 of the vacuum chamber 94 which is shown only in part. Shown inside reaction chamber 11 is a suitably confined radioactive, discharge, etc., source 14 of ionizing radiation which is preferably in the form of a plating or occluding on foil such as gold, platinum, or nickel, or alternatively a direct plating on the interior surface of the reaction chamber 11, or a sharp point or needle from which a corona discharge emanates. Suitable sources 14 of ionizing radiation include $^{63}$Ni in quantities up to 100 mCi activity and $^3$H in quantities up to 10 Ci activity, among others. Reaction chamber 11 includes a flange 200 which is sealed relative to chamber wall 10 via a suitable gasket 20 which is preferably an elastomer O-ring, or alternatively a metal O-ring, or a pressurized tubing metal O-ring, or a gasket arrangement of the conflat type, or any of a number of other demountable arrangements generally known in the art. Provision is made for heating or cooling the reaction volume via thermocouple monitored feedback control, the heating or cooling devices being here depicted as a band device 72 and an annular disk device 74. Inside the vacuum region of chamber 94 is shown a simple collecting electrode 16 connected, via a vacuum feedthrough 17 connection, to electrical instruments which suitably bias the electrode 16 to collect negative ions and which measure the current thereof.

In operation, a gas enters the inlet of the reaction chamber 11, as indicated by arrow 15, where it is subjected to an ionizing source 14 and the gas and plasma mixture thus provided in chamber 11 is drawn through the pinhole aperture of the type previously described into the interior of chamber 94 which may be maintained at a low absolute pressure by means of apparatus as described with reference to FIGS. 1 and 2. Electrode 16 is suitably biased to collect negative ions, and accordingly the negative ions flow from aperture 12 while the electrons in the flow diffuse into the walls of the aperture thus destroying the plasma, as such. Electrically biased electrode 16 then receives most ions passing through aperture 12 and the resulting current is determined in a manner well known to the art.

In FIG. 4 two improvements are depicted, the first being the addition of a source of a magnetic field, a solenoidal coil 21, with suitable electrical feedthroughs 75 and 76, which is used as an electromagnet. Alternatively, a suitable configuration of one or more permanent magnets may be employed. Coil 21 serves the purpose of suppressing collection of residual electrons escaping through the aperture. The second improvement is the replacement of the solid electrode 16 (FIG. 3) with a mesh electrode 23 in order to subtend a large solid angle for efficient ion collection while minimizing interference with gas flow and the efficient operation of the vacuum system.

The operation of the apparatus illustrated in FIG. 4 is essentially the same as that described with reference to FIG. 3 except that aperture 12 may be somewhat larger in view of the suppression of electrons passing therethrough into chamber 94 by coil 21. Again, with mesh electrode 23 properly biased, it receives most of the negative ions whereby a current is generated to provide the desired information relative to the quantity of such ions.

Figure 5:
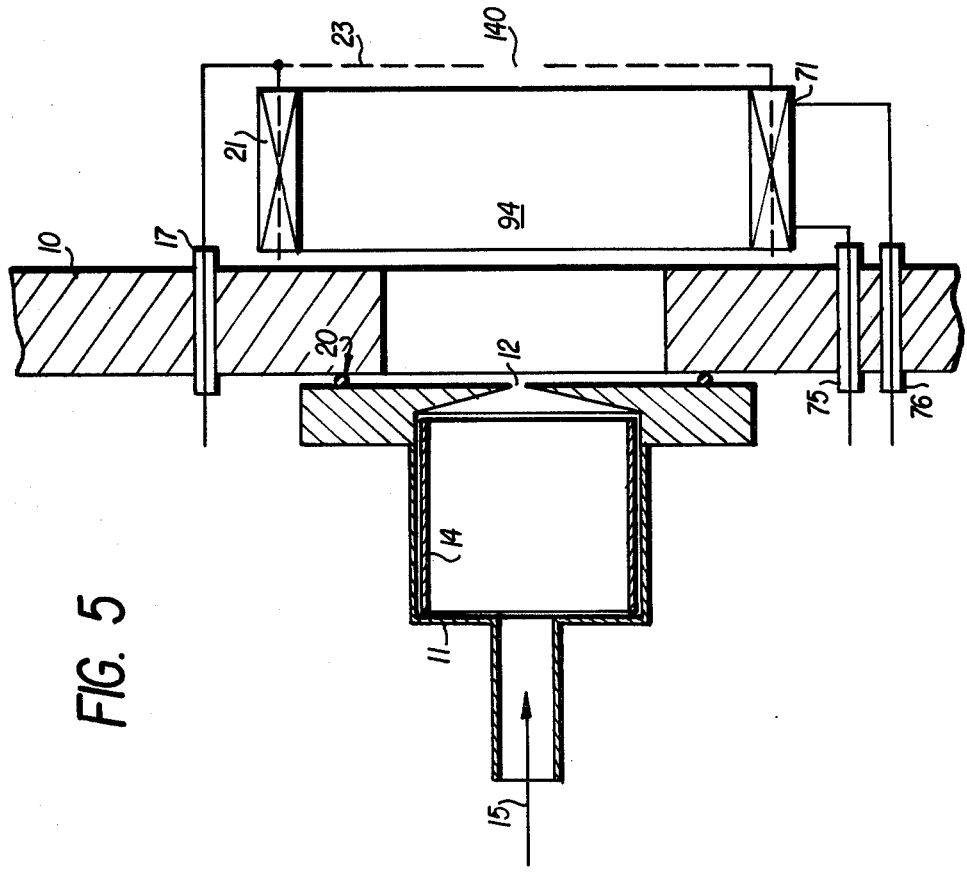
FIG. 5 is diagrammatic representation of a similar form of the invention in which an axial hole is provided in the collection electrode, whereby electrons, which are confined by the axial magnetic field to paths close to the axis, pass through the hole into the collection electrode and thus escape collection and erroneous interpretation as negative ions.

In FIG. 5 an improvement is disclosed in a modification of the apparatus shown in FIG. 4 whereby an axial hole 140 approximately 1 mm to 1 cm in diameter is provided in the collection electrode 23, so that electrons, confined by an axial magnetic field provided by coil 21 to paths near the axis, pass through the collection electrode 23 and escape collection.

Figure 6:
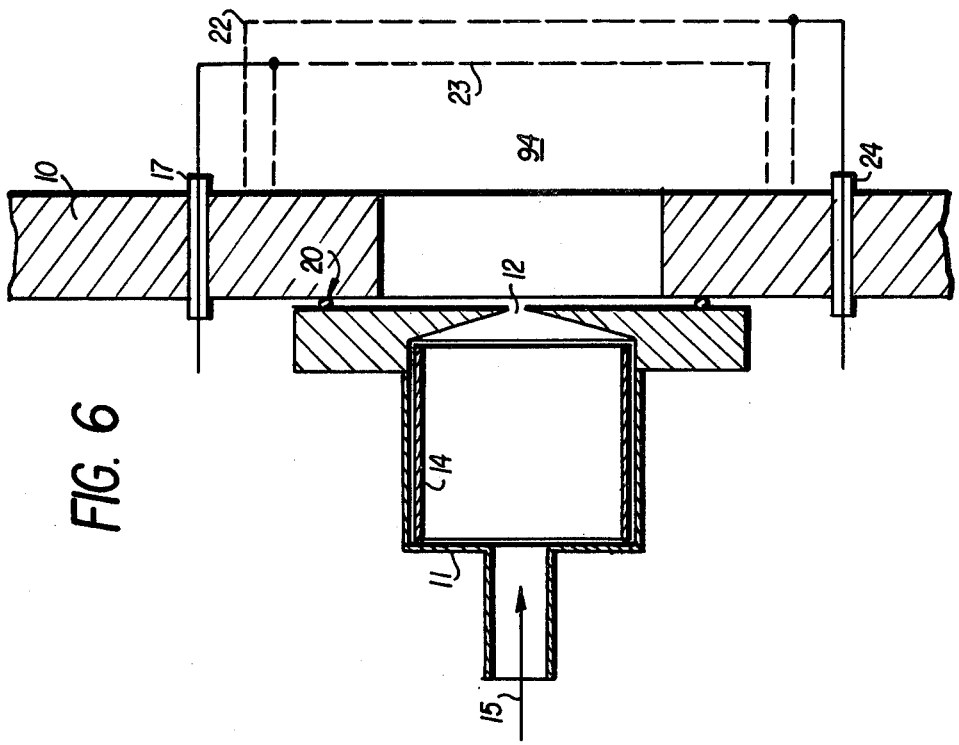
FIG. 6 is a diagrammatic representation of a similar form of the invention in which two concentric electrodes are employed, the inner one serving as an ion collector and the outer one as an electrostatic shield repelling back toward the inner electrode any ions passing through the inner mesh, as well as to collect and dispose of any ions of the opposite sign which may find their way to the vicinity of the inner electrode.

A further improvement is illustrated in FIG. 6, whereby a second mesh electrode 22 and electrical feedthrough 24 are added, electrode 22 being a repeller electrode electrically biased whereby negative ions that pass through the collection electrode 23 without being collected are repelled by electrode 22 and returned to electrode 23 for collection.

Figure 7:
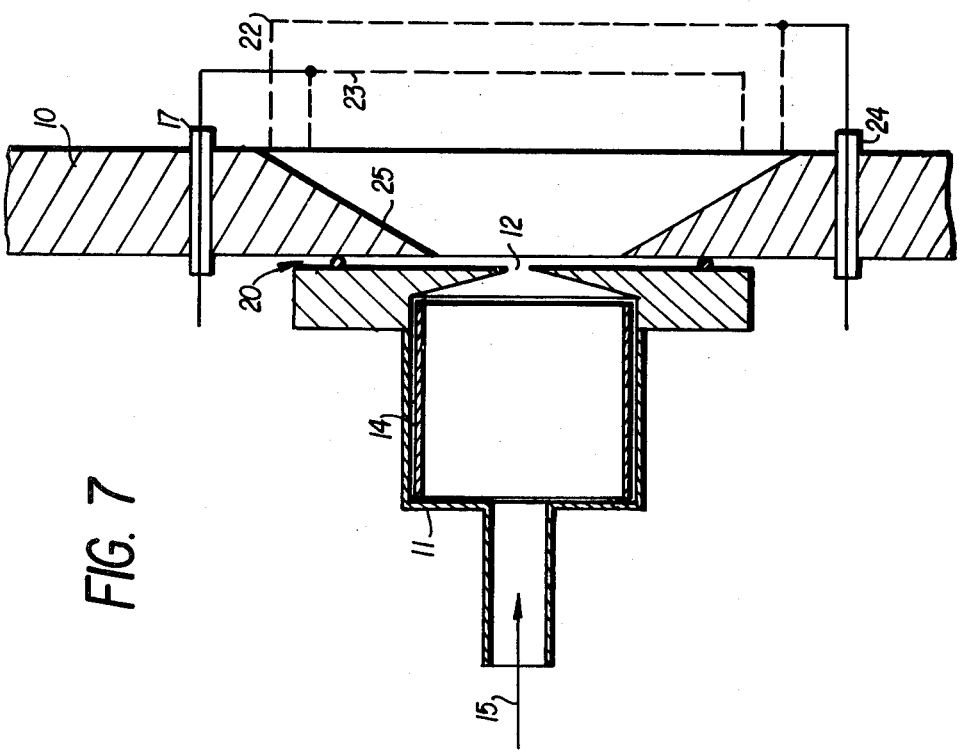
FIG. 7 is a diagrammatic representation of a similar form of the invention in which the inner wall of the vacuum chamber (or a flange attached thereto) is conically flared to provide a more aerodynamically favorable flow pattern for the carrier gas and entrained ions.

In FIG. 7 an additional improvement is depicted, whereby the interior surface 25 of the lower pressure chamber, part or all of which may also be an integral part or demountable part of reaction chamber 11, has a conical or otherwise flared shape thus maximizing the aerodynamic efficiency of the gas flow, and also controlling the shape of the electric field lines between vacuum chamber wall 10, collection electrode 23 and repeller electrode 22 whereby greater electrical efficiency of the ion collection process is obtained.

Figure 8:
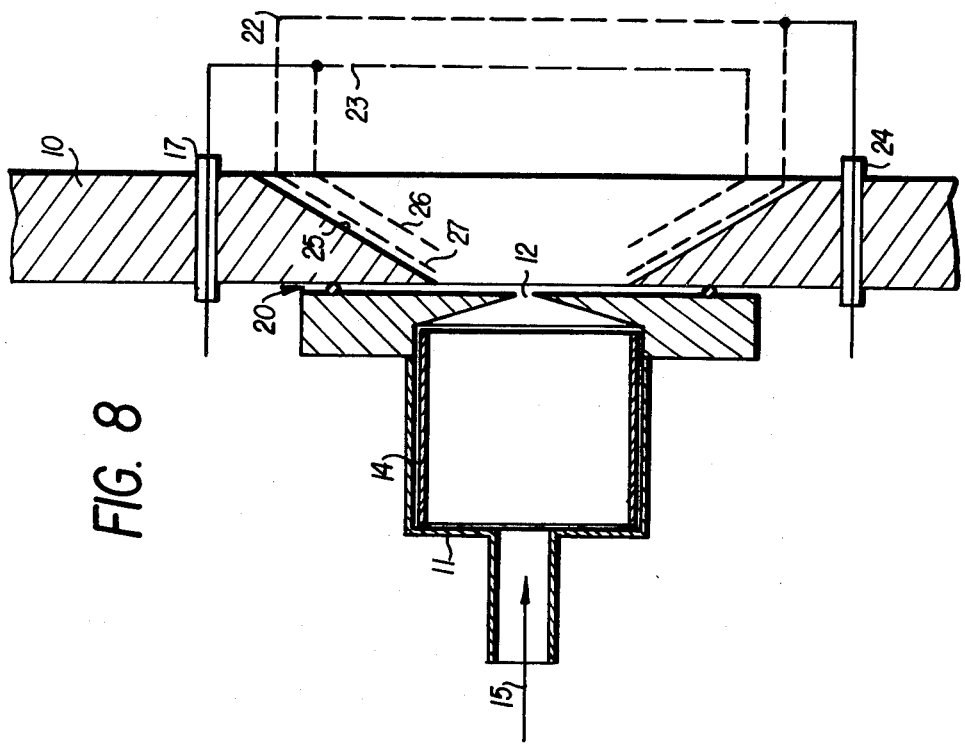
FIG. 8 is a diagrammatic representation of a similar form of the invention wherein collector and repeller electrodes are shaped to maximize the solid angle subtended as seen from the aperture and thus maximize collection efficiency.

An optional improvement is illustrated in FIG. 8 in which the collecting electrode 23 and/or the repeller electrode 22 are shaped to enclose by conical portions 26 and 27 respectively more fully the solid angle into which the gas flows, thus further increasing the efficiency of the ion collection process.

In FIG. 9 an optional modification is shown wherein collection electrode 16 or 23, as heretofore disclosed, is replaced by a particle multiplier 30 equipped with appropriate electrical leads and feedthroughs 31, to establish the ion collection bias potential, and 32 to establish the voltage across the multiplier providing its current gain. Further, an anode 34 and its feedthrough 35 for the collection of electron current or pulses in proportion to the arrival of ions at the particle multiplier face are provided. This optional form of the invention is primarily useful where the negative ion current is extremely small. A high vacuum of at least $10^{-5}$ torr is maintained in chamber 94. In operation, ionization of the sample molecules and gas takes place in reaction chamber 11 and a mixture of gas, ions and electrons pass through the orifice 12 wherein the electrons are separated by the phenomena heretofore described and the negative ions proceed to the particle multiplier 30 wherein the resulting charge or current is multiplied in a manner well known in the art. The multiplied current finally is received by anode 34 to produce a current having a predetermined proportional relationship to the charges received from the ions by the particle multiplier 35.

A modified embodiment is disclosed in FIG. 10 wherein additional electrodes, schematically depicted as a mesh cylinder 36 and an annular disk 37 with corresponding feedthroughs 40 and 42 are added for collecting and focussing onto the face of the particle multiplier 30 ions emerging from the aperture 12. Configurations as are schematically depicted by components 36 and 37 are referred to as a low pressure ion focus lens. This embodiment operates essentially the same as the embodiment discussed above with reference to FIG. 9 except that the ion flow from aperture 12 is focused to ensure its receipt by particle multiplier 30.

FIG. 11 illustrates a simplified general embodiment wherein low pressure chamber 94 is divided by a wall 121 into two subchambers individually and separately hermetically sealed and evacuated, the first subchamber 94a by vacuum pumping system 117 and the second subchamber 94b by vacuum pumping system 120, the two subchambers 94a and 94b being joined by a differential pumping aperture 122 of diameter in the approximate range of 1 mm to 1 cm. In this embodiment the first subchamber 94a is maintained at a pressure in the range $5 \times 10^{-5}$ torr to $5 \times 10^{-3}$ torr, which pressure range is suitable for the operation of focusing optics 110 via feedthroughs 111, but is not sufficiently low for the operation of particle multipliers and other devices such as mass spectrometers. The second subchamber 94b is maintained at a pressure of approximately $10^{-5}$ torr or less, and preferably $10^{-6}$ torr or less, such pressure being suitable for operation of a particle multiplier 115 via feedthroughs 116, and this pressure also being suitable for the operation of optional additional apparatus 112 via feedthroughs 114. Apparatus 112, if employed, comprises a mass spectrometer device, preferably but not exclusively, one of the quadrupole mass filter type.

The apparatus shown in FIG. 11, in operation, receives a carrier gas flow into the reaction chamber 90 wherein it is subjected to radiation and becomes a plasma with ions and electrons. This plasma passes through aperture 92 and is appropriately focused by optics 110 whereby it passes through an additional aperture 122, the electrons being separated as heretofore described from the ions passing through such apertures. The ion stream then proceeds through the apparatus 112 to the particle multiplier 115 wherein the charges resulting from the ions are multiplied and collected to provide a current proportional to the ionization current as heretofore described with reference to FIGS. 9 and 10. If apparatus 112 comprises a mass spectrometer, then the ions entering same are segregated in accordance with their mass-charge ratio and only those of selected mass-charge ratio are received by the particle multiplier 115. Inasmuch as the mass filter may be appropriately modulated to scan a large range of mass-charge conditions, the ions received in the subchamber 94b may, accordingly, be subjected to accurate and valuable analysis.

Figure 12:
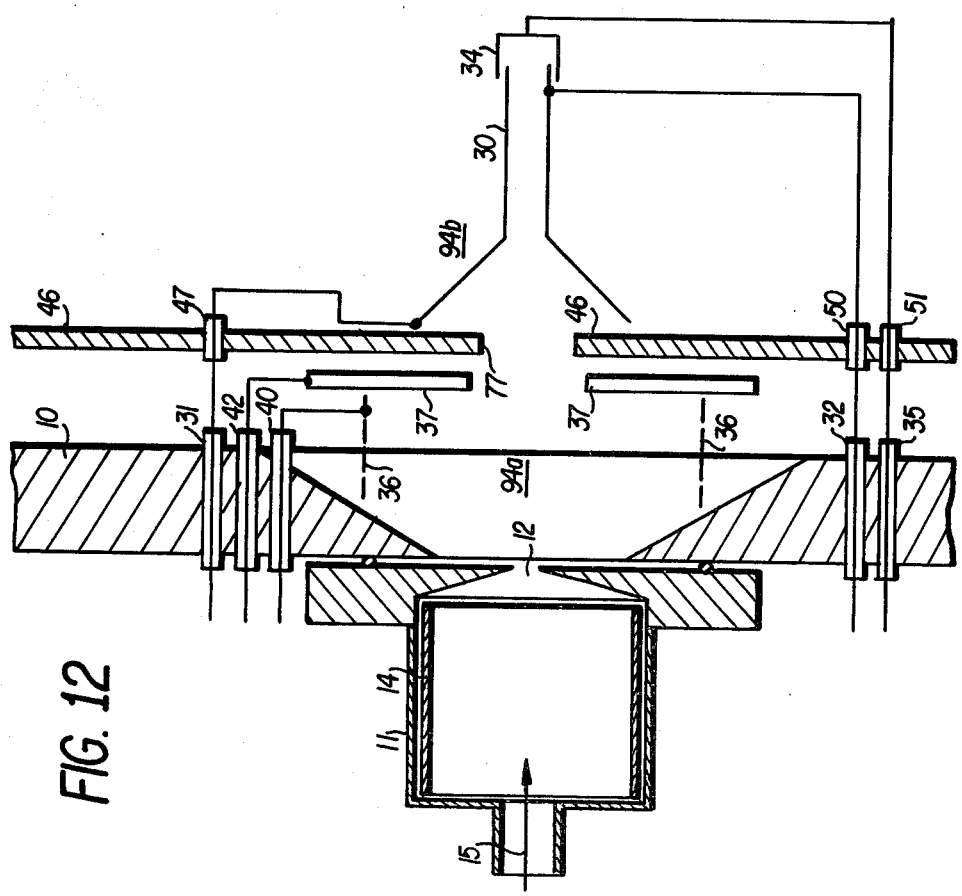
FIG. 12 is a diagrammatic representation of a similar form of the invention wherein the particle multiplier is separated from the focussing optics by a differential pumping aperture, the subchamber in which the particle multiplier is located being maintained by vacuum pumps at a pressure of $10^{-5}$ torr or less thus permitting use of the particle multiplier at high voltages and thus larger gains.

An improvement is depicted in FIG. 12 wherein a dividing wall 46 is placed in the low pressure region between the low pressure ion focus lens 36 and 37 and the particle multiplier 30 for providing, via vacuum pumping on subchamber 94b in which multiplier 30 is located, a lower pressure that can be practically maintained in the main chamber containing the low pressure ion focus lens 36 and 37. The purpose of this improvement is to allow operation of the particle multiplier 30 in a vacuum pressure regime most suitable to preserve its efficiency and usable lifetime.

The apparatus disclosed in FIG. 12 is similar to that of FIG. 11 except that no provision is made for a mass spectrometer 112 or the like. In operation, the device performs in essentially the same manner as that described with reference to FIG. 10 except that it is necessary to maintain a high vacuum only in subchamber 94b.

Figure 13:
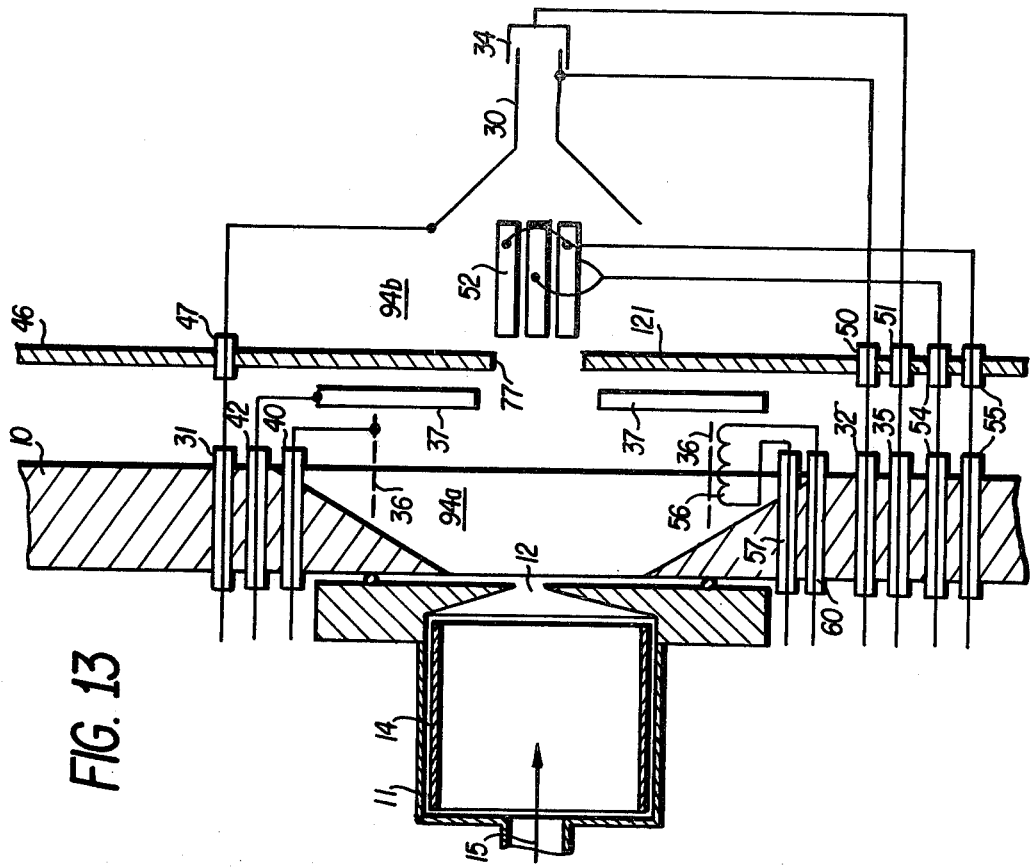
FIG. 13 is a diagrammatic representation of a similar form of the invention wherein the differential pumping aperture and the particle multiplier are separated by a mass analysis device, here depicted as a quadrupole mass filter, allowing mass analysis and identification of the ions being detected. Also shown is a filament or cathode appropriately placed with respect to the ion optics so that it may from time to time be used to produce ions by electron bombardment for the purpose of analyzing by positive or negative ion mass spectrometry those trace components of the carrier gas which do not respond well in an electron capture detector.

In FIG. 13 a mass analyzing device, here depicted as a quadrupole mass filter 52 with associated electrical feedthroughs 54 and 55 to provide the dc and rf potentials required for its operation, is inserted between the differential pumping aperture 77 in wall 121 (which divides chamber 94 into subchambers 94a and 94b in a manner heretofore described) and the particle multiplier 30. Identification and quantification is thus provided by mass spectrometry of the positive and negative ion species emerging from aperture 12. Also included is a cathode or filament 56 and its associated feedthroughs 57 and 60, its purpose being to produce, by electron impact, positive and negative ions of the neutral gas molecules. Such ions are focused by lens 36 and 37, analysed as to mass by filter 52 and selectively collected, detected and registered by multiplier 30. This modification permits detection of sample molecules in the carrier gas which have not been ionized or have been ionized inefficiently in the reaction chamber 11.

An optional version of the invention is illustrated in FIG. 14 wherein, via spaced insulators 61 and 65, reaction chamber 11 is electrically isolated from the vacuum system wall 10 and the carrier gas supply 15. By this means, reaction chamber 11 is established at a selected convenient potential via connection 66 to facilitate operation of the detection system comprised of electrodes 16, or, as applied to other embodiments, components designed by reference numerals 23, or 22 and 23, or 26 and 27, or 30, or 36 and 37 and 30, or 36 and 37 and 77 and 30, or 36 and 37 and 77 and 52 and 30, and their associated electronic instrumentation, which then may be referenced to ground potential or another potential different than the potential established at reaction chamber 11 via connection 66.

In FIG. 15 there a further optional version of the invention is depicted in which, in addition to the features shown in and discussed under FIG. 14 above, a feedthrough 70 and an additional electrode 67 are provided, the latter being shown as an axial wire. This modification serves the purpose of operating the ECD in one of its traditional current collecting modes concurrently with, or instead of, the mode described herein.

Although preferred embodiments of the invention are described above, it is to be understood that the invention is capable of other adaptations and modifications within the scope of the appended claims.

Having thus described my invention, what I claim as new and desire to secure by Letters Patent of the United States is:

1. A method of measuring concentrations of sample molecules in a carrier gas which comprises the steps of forming a carrier gas-sample molecule mixture with a mixture of a concentration of free electrons and sample molecule ions, removing substantially all of said free electrons from said ions, and collecting and measuring said ions, said ion measurement being proportional to the sample molecule concentration in the carrier gas, said forming step occurring in a first region having an absolute pressure the range of 0.1 torr to 100 atmospheres and said collecting step occurring in a second region having a lower pressure than said first region.

2. A method in accordance with claim 1, wherein said second region is maintained at a pressure of $10^{-5}$ torr or less.

3. A method in accordance with claim 1, wherein said ions are moved from said first region to said second region in said carrier gas.

4. A method in accordance with claim 1, wherein said ions are moved between said forming step performed in said first region and said collecting step performed in said second region by an electrostatic field.

5. A method in accordance with claim 1 wherein a wall is provided between said first and second regions, an aperture of conductive material being provided in said wall through which said ions are caused to flow with a plasma at least to said wall.

6. A method in accordance with claim 5 wherein said aperture has an effective diameter and thickness less than the Debye length characteristic of said plasma.

7. A method in accordance with claim 6 wherein said aperture has a diameter and thickness each less than 50 $\mu$m.

8. A method in accordance with claim 7, wherein said aperture has a diameter and thickness of about 25 $\mu$m.

9. A method in accordance with claim 5 wherein said aperture is provided with dimensions whereby most electrons received therein diffuse into the walls of the aperture and most of said ions pass therethrough thereby substantially destroying said plasma.

10. A method in accordance with claim 1, wherein the pressure in said second region is maintained sufficiently low to preclude substantial recombination of the negative sample molecule ions and the positive ions in said carrier gas.

11. A method in accordance with claim 10 wherein a particle multiplier is provided in said second region, said multiplier being electrically biased to attract ions of one predetermined polarity to its cathode, said multiplier collecting and multiplying the current of said ions received by said cathode.

12. A method in accordance with claim 11 wherein said ions are negative ions.

13. A method in accordance with claim 11, wherein said said ions are positive ions.

14. A method in accordance with claim 11, wherein an magnetic field is establishing relative to said ion flow towards said cathode which performs the function of effectively preventing substantially all electrons in the vicinity of said ion flow from reaching said cathode.

15. A method in accordance with claim 14 wherein said magnetic field causes said electrons to travel paths whereby their probability of recombination with positive ions is substantially increased.

16. A method in accordance with claim 14 wherein said magnetic field causes said electrons to be received by a surface electrically isolated from said cathode.

17. A method in accordance with claim 11 wherein the ion flow towards said particle multiplier is focused by at least one electrostatic lens.

18. A method in accordance with claim 17 wherein said electrostatic lens is positioned prior to said second region.

19. A method in accordance with claim 18, wherein said ion flow between said electrostatic lens and said cathode is subjected to a mass-charge filtering step.

20. A method in accordance with claim 19, wherein neutral gas molecules in said ion flow are selectively subjected to an electron bombardment prior to said filtering step to provide further analysis of the constituent materials of the carrier gas and sample molecules.

21. In combination with an electron capture detector which includes high energy electron producing means as a source of ionization in a region provided therefor, a chamber and means for maintaining said chamber at a lower relative operating pressure than said electron capture detector, aperture means interfacing said electron capture detector with said chamber for receiving an ion flow therethrough into said chamber, electron removal means for removing electrons from said ion flow after entering said aperture means, an ion collection and measuring means associated with said chamber for measuring ions flowing from the electron capture detector into said chamber.

22. Apparatus in accordance with claim 21, wherein said ionization region is free from externally imposed electrostatic fields and means for measuring electron current.

23. A method of measuring concentrations of sample molecules in a carrier gas which comprises the steps of forming a carrier gas-sample molecule mixture with a mixture of a concentration of free electrons and sample molecule ions, removing substantially all of said free electrons from said ions, and collecting and measuring said ions, said ion measurement being proportional to the sample molecule concentration in the carrier gas, an electrode being provided for collecting said ions, said electrode being electrically biased to attract negative ions and providing a conductor leading to means measuring current from said ions attracted thereto, said electrode comprising a mesh whereby non-charged particles pass therethrough without causing obstruction of said negative ions, a further electrode which encloses at least in part said mesh, said further electrode provided with an electrical bias whereby it repels negative ions passing through said mesh without being collected whereby they are urged back towards said mesh for collection.

24. A method of measuring concentrations of sample molecules in a carrier gas which comprises the steps of forming a carrier gas-sample molecule mixture with a mixture of a concentration of free electrons and sample molecule ions, removing substantially all of said free electrons from said ions, and collecting and measuring said ions, said ion measurement being proportional to the sample molecule concentration in the carrier gas, an electrode being provided for the collecting of said ions, said electrode being electrically biased to attract positive ions and providing a conductor leading to means measuring current from said ions attracted thereto, said electrode comprising a mesh whereby non-charged particles pass therethrough without causing obstruction to said positive ions.

25. A method in accordance with claim 24 wherein a further electrode encloses at least in part said mesh, said further electrode provided with an electrical bias whereby it repels positive ions passing through said mesh without being collected whereby they are urged back towards said mesh for collection.

26. Apparatus for measuring concentrations of sample molecules in a carrier gas which comprises
ionization means in a first region of the apparatus for producing a carrier gas-sample molecule mixture containing a concentration of free electrons and sample molecule ions,
ion collection and measurement means in a second region for receiving an ion flow from said ionization means disposed between said first and second regions, said ion collection and measurement means comprising an electrode which is electrically biased to attract said ions and which comprises a mesh,
electron removal means associated with the ion flow from said ionization means to said ion collection and measurement means for substantially removing electrons from said ion flow prior to the receipt of said ions by said collection and measurement means, and
pressure differential producing means for maintaining a relatively lower pressure in said second region than in said first region.

27. Apparatus in accordance with claim 26, wherein a further electrode is provided which at least in part surrounds said first mentioned electrode, said electrodes being electrically biased relative to each other whereby ions attracted by said first mentioned electrode are repelled by said second mentioned electrode.

28. Apparatus for measuring concentrations of sample molecules in a carrier gas which comprises
ionization means in a first region of the apparatus for producing a carrier gas-sample molecule mixture containing a concentration of free electrons and sample molecule ions,
ion collection and measurement means in a second region for receiving an ion flow from said ionization means disposed between said first and second regions, said ion collection and measurement means comprising a particle multiplier,
electron removal means associated with the ion flow from said ionization means to said ion collection and measurement means for substantially removing electrons from said ion flow prior to the receipt of said ions by said collection and measurement means, and
pressure differential producing means for maintaining a relatively lower pressure in said second region than in said first region.

29. Apparatus in accordance with claim 28, wherein biasing and power means are provided for said particle multiplier whereby it can selectively collect and measure positive ions or negative ions.

30. Apparatus in accordance with claim 28, wherein an electrostatic lens component is disposed between said ion flow passage flow means and said particle multiplier for focusing the ion flow for receipt by said particle multiplier.

31. Apparatus in accordance with claim 30, wherein a wall with a differential pumping opening for said ion flow is disposed between said electrostatic lens component and said particle multiplier, and vacuum producing means is provided for maintaining said particle multiplier in a high vacuum suitable for its efficient operation.

32. Apparatus in accordance with claims 31, wherein a mass analysis device is situated between said opening and said particle multiplier for performing the function of identifying and quantifying the nature of the ions being detected.

33. Apparatus in accordance with claim 32, wherein said mass analysis device comprises a quadrupole mass filter.

34. Apparatus in accordance with claim 33, wherein electron emission means is disposed in the vicinity of said electrostatic lens adapted selectively to bombard and ionize material in said ion flow not previously ionized for identification and quantification thereof by said mass analysis device.

35. Apparatus for measuring concentrations of sample molecules in a carrier gas which comprises
ionization means in a first region of the apparatus for producing a carrier gas-sample molecule mixture containing a concentration of free electrons and sample molecule ions,
ion collection and measurement means in a second region for receiving an ion flow from said ionization means disposed between said first and second regions,
electron removal means associated with the ion flow from said ionization means to said ion collection and measurement means for substantially removing electrons from said ion flow prior to the receipt of said ions by said collection and measurement means, said electron removal means comprising a magnetic field producing means which subjects said ion flow to a magnetic field adapted to remove free electrons from said flow, and
pressure differential producing means for maintaining a relatively lower pressure in said second region than in said first region.

36. Apparatus for measuring concentrations of sample molecules in a carrier gas which comprises
ionization means in a first region of the apparatus for producing a carrier gas-sample molecule mixture containing a concentration of free electrons and sample molecule ions,
ion collection and measurement means in a second region for receiving an ion flow from said ionization means disposed between said first and second regions,
electron removal means associated with the ion flow from said ionization means to said ion collection and measurement means for substantially removing electrons from said ion flow prior to the receipt of said ions by said collection and measurement means, said electron removal means comprising an electrically conductive aperture in said flow passage means, said aperture having an effective diameter and thickness less than the Debye length characteristic of the plasma in which said ion flow is contained up to said aperture, whereby the electrons substantially diffuse into the walls of said aperture and the ions substantially pass through said aperture, and pressure differential producing means for maintaining a relatively lower pressure in said second region than in said first region.

37. Apparatus in accordance with claim 36, wherein said ionization means comprises high energy electron producing means.

38. Apparatus in accordance with claim 37, wherein said high energy electron producing means comprises a corona discharge device.

39. Apparatus in accordance with claim 37, wherein said high energy electron producing means comprises $^{63}Ni$.

40. Apparatus in accordance with claim 39, wherein said ionization means comprises alpha particle producing means.

41. Apparatus in accordance with claim 37, wherein said high energy electron producing means comprises $^{3}H$.

42. Apparatus in accordance with claim 36, wherein said ionization means comprises gamma-ray producing means.

43. Apparatus in accordance with claim 36, wherein said ionization means comprises photon producing means.

* * * * *